(12) United States Patent
Plassky et al.

(10) Patent No.: US 10,117,712 B2
(45) Date of Patent: Nov. 6, 2018

(54) MODULAR NAVIGATION REFERENCE

(71) Applicant: Brainlab AG, Munich (DE)

(72) Inventors: Norman Plassky, Erfurt (DE);
Hansjoerg Huber, Bodolz (DE)

(73) Assignee: Brainlab AG, Munich (DE)

( * ) Notice: Subject to any disclaimer, the term of this patent is extended or adjusted under 35 U.S.C. 154(b) by 559 days.

(21) Appl. No.: 14/430,918

(22) PCT Filed: Sep. 25, 2012

(86) PCT No.: PCT/EP2012/068843
§ 371 (c)(1),
(2) Date: Mar. 25, 2015

(87) PCT Pub. No.: WO2014/048448
PCT Pub. Date: Apr. 3, 2014

(65) Prior Publication Data
US 2015/0257851 A1 Sep. 17, 2015

(51) Int. Cl.
*A61B 5/00* (2006.01)
*A61B 19/00* (2006.01)
*A61B 90/00* (2016.01)
*A61B 34/20* (2016.01)

(52) U.S. Cl.
CPC .............. *A61B 19/54* (2013.01); *A61B 90/39* (2016.02); *A61B 2034/2055* (2016.02); *A61B 2090/3983* (2016.02); *A61B 2090/3987* (2016.02)

(58) Field of Classification Search
CPC . A61B 19/54; A61B 90/39; A61B 2090/3987; A61B 2090/3983; A61B 2034/2055
See application file for complete search history.

(56) References Cited

U.S. PATENT DOCUMENTS

| 2004/0138556 A1 | 7/2004 | Cosman |
| 2005/0245820 A1 | 11/2005 | Sarin |
| 2007/0100325 A1 | 5/2007 | Jutras et al. |
| 2012/0123299 A1 | 5/2012 | Neubauer et al. |

FOREIGN PATENT DOCUMENTS

| DE | 20 2004 011567 | 11/2004 |
| DE | 20 2007 010078 | 10/2007 |
| DE | 10 2007 014737 | 9/2008 |
| EP | 0 591 712 | 4/1994 |

OTHER PUBLICATIONS

International Search Report and Written Opinion for International Application No. PCT/EP2012/068843 dated Jun. 21, 2013.

*Primary Examiner* — Joel Lamprecht
(74) *Attorney, Agent, or Firm* — Tucker Ellis LLP (57) ABSTRACT

A medical marker device comprising a) a plurality of markers which are disposed on the marker device such that each marker of the plurality of markers displays mirror symmetry with respect to a mirror plane of symmetry which is common to all markers of the plurality of markers, b) an attaching unit for attaching the marker device to a marker holder, wherein the attaching unit is disposed on the mirror plane of symmetry.

12 Claims, 10 Drawing Sheets

MODULAR NAVIGATION REFERENCE

RELATED APPLICATION DATA

This application is a national phase application of International Application No. PCT/EP2012/068843 filed Sep. 25, 2012 and published in the English language.

The present invention is directed to a medical marker device in accordance with claim 1, a marker system comprising the marker device and a marker holder, a data processing method of determining a reference plane in a navigated procedure which uses the marker device or marker system, respectively, and a program comprising instructions corresponding to the data processing method.

Marker devices are used in navigated procedures such as neurosurgery, joint surgery, pharmaceutical tumor treatment and radio therapy for determining positional information of objects having a predetermined and preferably fixed position relative to the marker device. Such marker devices are often attached to fragile bony structures. A risk arising therefrom is that a bulky and heavy marker device may exert a torque on the bony structure, thereby damaging the bony structure in an undesired manner and endangering the reliability of position determination by loosening its attachment to the bony structure.

Known marker devices include reference stars which essentially comprise a holding unit and carrying units sticking out from the holding unit which carry at least three individual markers to support determination of a position which is defined in three dimensions and the object orientation in space. As a consequence, such a reference star tends to be both bulky and heavy, thereby potentially leading to a mechanical torque exerted on the bony structure and also impairing user-friendliness due to its comparably large size.

A problem to be solved by the present invention therefore is to provide a marker device which is light in weight and small in size, which in particular supports reliable position determination in three dimensions and object orientation in space.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The method in accordance with the invention is in particular a data processing method. The data processing method is preferably performed using technical means, in particular a computer. Preferably, the inventive method is at least partly executed by a computer. That is, all steps or just some of the steps (i.e. less than a total number of steps) of the inventive method may be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The invention is preferably directed to a medical marker device. The medical marker device is suitable for use in in particular a navigated procedure, in particular a navigated medical procedure. The medical marker device preferably comprises a plurality of markers which are disposed on the marker device such that each of the markers of the plurality of markers displays mirror symmetry with respect to a mirror plane of symmetry which is common to all markers of the plurality of markers. It is the function of a marker to be detected by a marker detection device (for example, a camera or an ultrasound receiver or analytical devices, like CT or MRI), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic shape or planar (i.e. flat) shape.

A marker device can for example be a device such as a supporting (holding) structure which supports (holds) one marker or more than one (individual) markers which are preferably in a predetermined spatial relationship. A marker device comprises one, two, three or more markers which are in case of two or more markers in a predetermined spatial relationship. This predetermined spatial relationship is in particular known to a navigation system and for example stored in a computer of the navigation system.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of the markers relative to each other. It is therefore also then possible for the objects (for example, instruments and/or parts of a body) to which the reference star is attached to be identified and/or differentiated. In a surgical navigation method, the reference star serves to attach a plurality of markers to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

A navigation system, in particular a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) in particular comprises a processor (CPU), a working memory, advantageously an indicating device for issuing an indication signal (for example, a visual indicating device such as a monitor and/or an audio indicating device such as a loudspeaker and/or a tactile indicating device such as a vibrator) and advantageously a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

The plurality of markers comprises preferably at least two, in particular exactly two markers. Preferably, the markers each comprise a planar (i.e. flat) marker surface. However, other surface geometries of the markers such as curved surfaces are also in the framework of the invention. The marker surface is understood to comprise or be the surface which reflects or emits electromagnetic radiation towards a detection device of a navigation system which is used to determine the position of the marker. For example, the marker surface may be the free surface of a foil (in particular, a foil reflecting or emitting electromagnetic waves for use by a navigation system) having corresponding properties or of a three-dimensional body such as a sphere (marker sphere). The marker surface may not only in the case of a marker sphere be curved. Rather, a marker foil may also be disposed in a concave geometry which opens with the concave side into free space. For example, a marker carrying unit may have a concave portion in it to which the marker foil is attached (for example, glued) in order to form a curved marker surface.

The circumference of the marker device may have a regular, in particular symmetric, or an irregular, in particular unsymmetric, shape. Preferably, the markers have a round or a polygonal circumference. For example, in the case of a marker device foil, the foil may be cut out in an elliptical, in particular circular, or cornered, in particular polygonal, shape.

Preferably, the markers are oriented in the same direction. This supports the detectability of all of the markers at the same time from the same hemisphere in which a detection device of a navigation system, in particular a single detection device, is located. In the case of a planar marker surface, the surface normals of the marker surfaces preferably are parallel and have the same orientation. In the case of a curved, in particular concave, marker surface, the surface normals of all of the markers surfaces in the apex of each concave marker surface preferably are parallel and have the same orientation.

Preferably, all of the markers are disposed parallel to a marker plane, in particular in the marker plane. A marker plane is understood to be a plane in which each one of the markers is at least partly disposed. More particularly, all of the markers have the same orientation relative to the marker plane in accordance with the above description regarding the markers being oriented in the same direction. In particular, the surface normals of the marker surfaces preferably all have the same orientation relative to the marker plane, in particular they all are perpendicular to the marker plane. If the markers comprise or consist of planar marker surfaces, the markers preferably are disposed completely in the marker plane. Generally, the term of marker plane is understood to denote a plane relative to which all of the markers have the same orientation.

According to another embodiment of the invention, at least one of the plurality of markers may be located outside of the marker plane. For example, flat markers having a surface normal perpendicular to the marker plane may be disposed parallel to one another and both parallel to the marker plane, wherein at least one of the flat markers is not even partly disposed in the marker plane.

According to an even further embodiment of the invention, the plurality of markers may consist of flat markers or markers having a curved marker surface, wherein the surface normals of all of the markers are parallel to each other and have the same (angular) orientation relative to the marker plane which in particular does not resemble a perpendicular orientation relative to the marker plane. In other words, all of the markers may be tilted with the same angle relative to the marker plane.

Further preferably, the surface normal of the marker plane is parallel to the mirror plane of symmetry and the marker plane is tilted relative to the mirror plane of symmetry at an angle of between 0° and 90°, excluding these values. Alternatively, the respective angle between the mirror plane of symmetry and the marker plane may be 90° such that the marker plane is perpendicular to the mirror plane of symmetry.

Preferably, the marker device comprises a marker carrier which is preferably planar. Further preferably, the markers are disposed on the marker carrier, in particular flat markers are disposed on the planar marker carrier, in particular a flat surface of the planar marker carrier. A planar marker carrier is understood to be a carrying unit for markers which has at least one flat surface. Further preferably markers may be disposed on opposite surface of the (planar) marker carrier, i.e. markers may be disposed on surfaces oriented towards each one half-space in directions opposite to each other by 180°.

Preferably, the marker device comprises an attaching unit for attaching the marker device to a marker holder, wherein the attaching unit is disposed on the mirror plane of symmetry. In particular, the attaching unit may be formed integrally or at least be attached to the marker carrier. The attaching unit in particular comprises a recess or clearance for receiving the marker holder. The marker holder preferably takes the form of a Schanz screw or drill with an AO interface (which is a standardized mechanical interface approved for commercial use and defined by the AO "Arbeitsgemeinschaft Osteosynthese") or a speed pin interface (offered and constructed by Brainlab AG) suitable in particular for a 3.2 mm speed pin. In particular, the longitudinal axis of such a pin, screw or drill lies in the mirror plane of symmetry if such a marker holder is connected to the attaching unit, in particular fitted into the recess or clearance. In such a case, the marker device can be rotated around the longitudinal axis of the marker holder when attached to the marker holder while maintaining the relative orientation of the axis of the marker holder and the mirror plane of symmetry. The recess or clearance in the attaching unit may in the case of a BL interface have a triangular cross-section with rounded corners. In the case of an AO interface, it may have a partially circular cross-section which is flattened off at one side by a straight line. At the locations at which the straight line intersects the circular circumferential line, corners and/or angles are formed.

The invention is also directed to a marker system comprising the marker device as described above and a marker holder configured to be connected with the attaching unit of the marker device, wherein the marker holder is in particular of elongate shape. The marker holder is in particular a rod comprising a fastening means for fastening the marker holder to an anatomical body part. The fastening means is at least one of an external screw thread and a clamp formed at one end of the rod. At the end of the rod to which the marker device is to be fitted, the rod preferably has a tri-angular cross-section (a BL interface) or an AO interface for inserting into the attaching unit of the marker device. The rod preferably is one of a speed pin, a Schanz screw or a drill.

The invention is also directed to a data processing method of determining a reference plane in a navigated procedure, in particular a navigated medical procedure, wherein the data processing is executed by a computer and comprises preferably the following features.

Preferably, marker position data comprising marker position information is acquired. The marker position information in particular describes a position of at least three markers of preferably two marker devices as described above or two marker systems as described above. The position of the at least three markers is in particular determined by using a navigation system operating on the principle of detection of electromagnetic radiation emitted or reflected from the markers. Preferably, the marker devices, in particular the marker systems, are fastened to an anatomical body part to which they preferably have a predetermined and in particular fixed position.

Preferably, reference plane data comprising reference plane information is determined based on the marker position data, in particular based on the marker position information. The reference plane information in particular describes a reference plane comprising positions of the at least three markers. For example, the computer of the navigation system is configured to compute a quadrangular or triangular surface, in the corners of which the at least three markers are located.

Such a surface may then be used to define a plane in which the surface lies as a navigational reference. In particular, such a plane may be used to determine the position or position change of anatomical body parts towards either side of the plane. In particular, the position of anatomical body parts may be determined relative to the plane and in particular the side of the plane which an anatomical body part is positioned can be determined according to the invention.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The aforementioned method, in particular any method step associated with or directed to fastening the marker system, in particular the marker holder, to an anatomical body part, does not involve an invasive step which would represent the substantial physical interference with the human or animal body requiring professional medical expertise to be carried out and entailing a substantial health risk even when carried out with the required professional care and expertise. Furthermore, no part of the inventive method involves a step of treating a human or animal body using surgery or therapy.

In the following, example embodiments of the present invention are described with reference to the figures which are nearly to be regarded as examples of the invention without limiting the invention to the specific embodiments.

Figure 1:
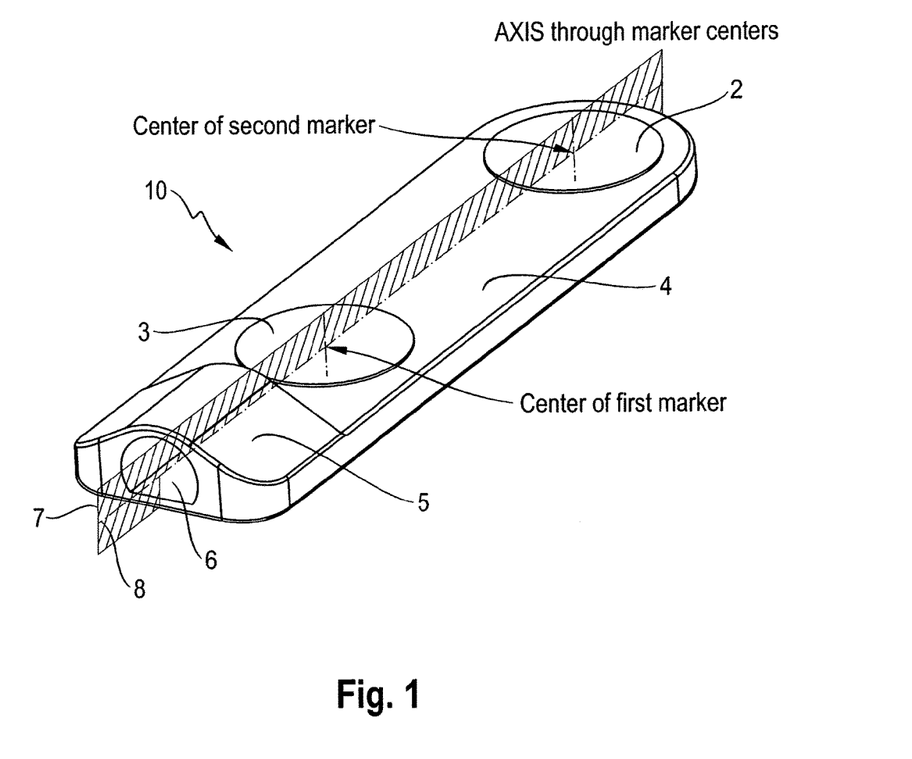
FIG. 1 shows a general layout of a marker device according to a first embodiment having a first type of attaching unit.

According to FIG. 1, the marker device 10c of the first embodiment of the invention has a marker carrier 1 with a planar marker surface on which two flat markers 2, 3 having a circular circumference are disposed. The marker device 10 comprises an attaching unit 5a protruding from the marker carrier 1 and having a clearance 6 of a first type formed as a longitudinal hole having a partly circular cross-section. The markers 2, 3 and the clearance 6 are disposed with their centre (in the case of the clearance 6, with its longitudinal axis) on the mirror plane of symmetry 7 (which is of infinite extent) which is represented by its trace 8 which is formed by intersecting the marker surface 4 with the mirror plane 7 (i.e. the trace 8 is the straight line which represents the set of prints at which the marker surface 4 intersects the mirror plane 7).

Figure 2:
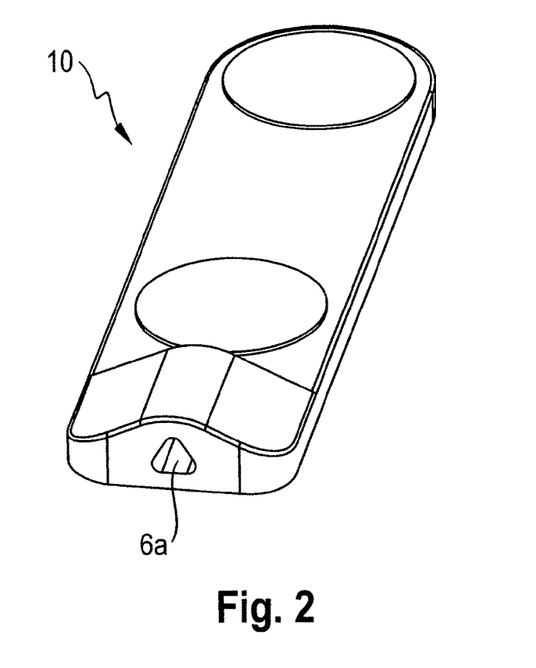
FIG. 2 shows the marker device of FIG. 1 having a second type of attaching unit.
Figure 3:
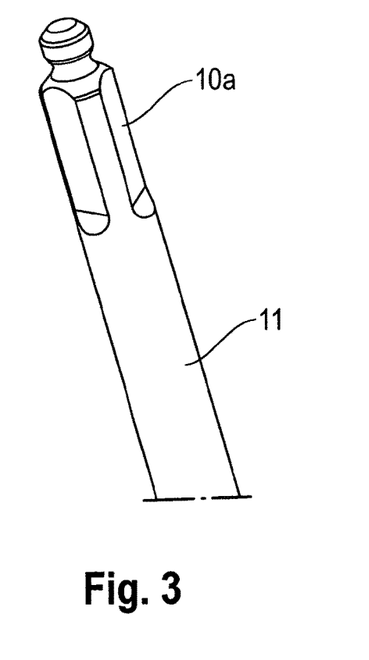
FIG. 3 shows a marker holder having an attaching end for a second type of attaching unit.

According to FIG. 2, the marker device 10 of the first embodiment may have a clearance 6a of a second type which has a triangular cross-section with rounded-off corners. This clearance 6a is suitable to fit on the attaching end 10a of an elongate marker holder 9 of BL speed pin type as shown in FIG. 3.

Figure 4:
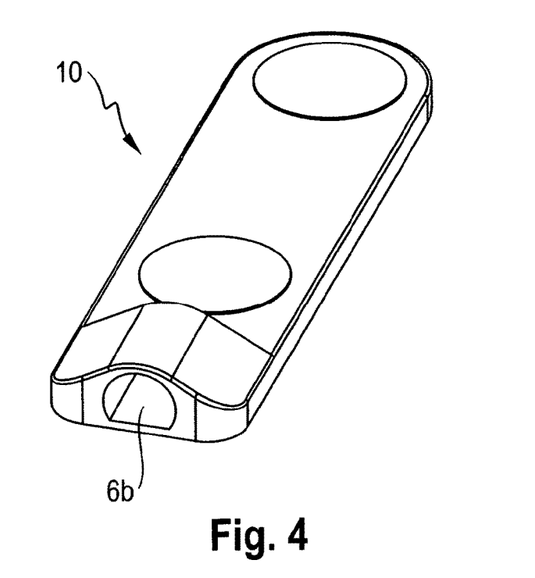
FIG. 4 shows the marker device of FIG. 1 having a first type of attaching unit.
Figure 5:
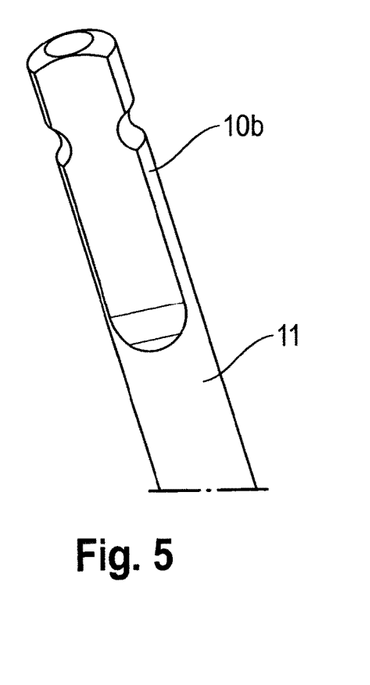
FIG. 5 shows the marker holder having an attaching end for first type of attaching unit.

FIG. 4 shows again the marker device 10 of the first embodiment with a clearance 6 of a first type which is suitable to fit the attaching end 10b of a marker holder 9 having an AO interface.

Figure 6:
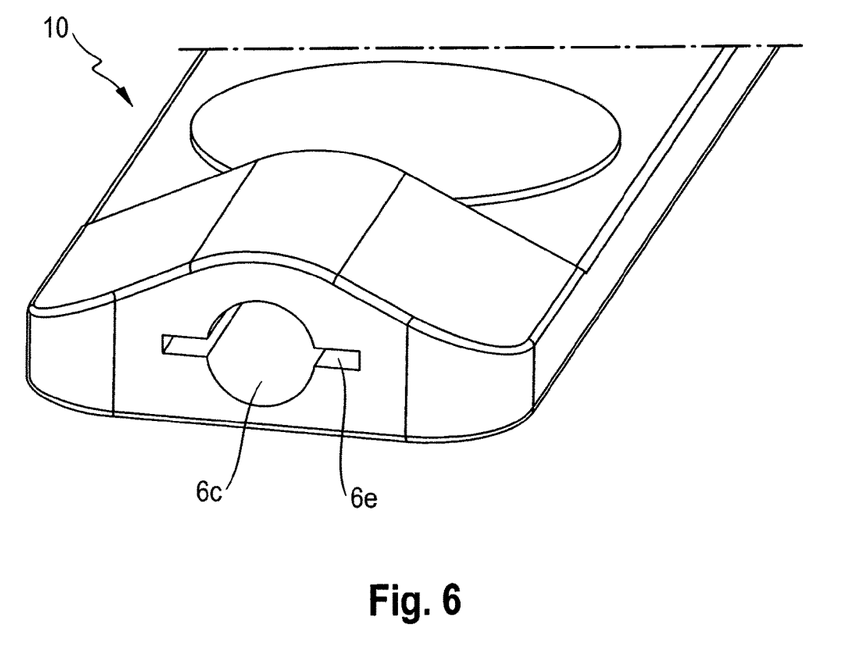
FIG. 6 shows the marker device of FIG. 1 having a third type of attaching unit supporting attaching units with round cross sections of defined diameter.

FIG. 6 shows the marker device 10 of the first embodiment having a clearance 6c of a third type being formed as a round hole with a longitudinal recess 6d on diametrically opposite sides of the hole which are suitable to widen the hole if a marker holder is inserted into the hole, which marker holder is slightly oversized with respect to the hole. Thereby a force fit between the attaching (insertion) end of the marker holder and the clearance 6c may be established to resist vibrations and therefore preventing undesired rotation of the embodiment on the marker holder in particular when exposed to typical surgical procedures such as drilling or sawing.

Figure 7:
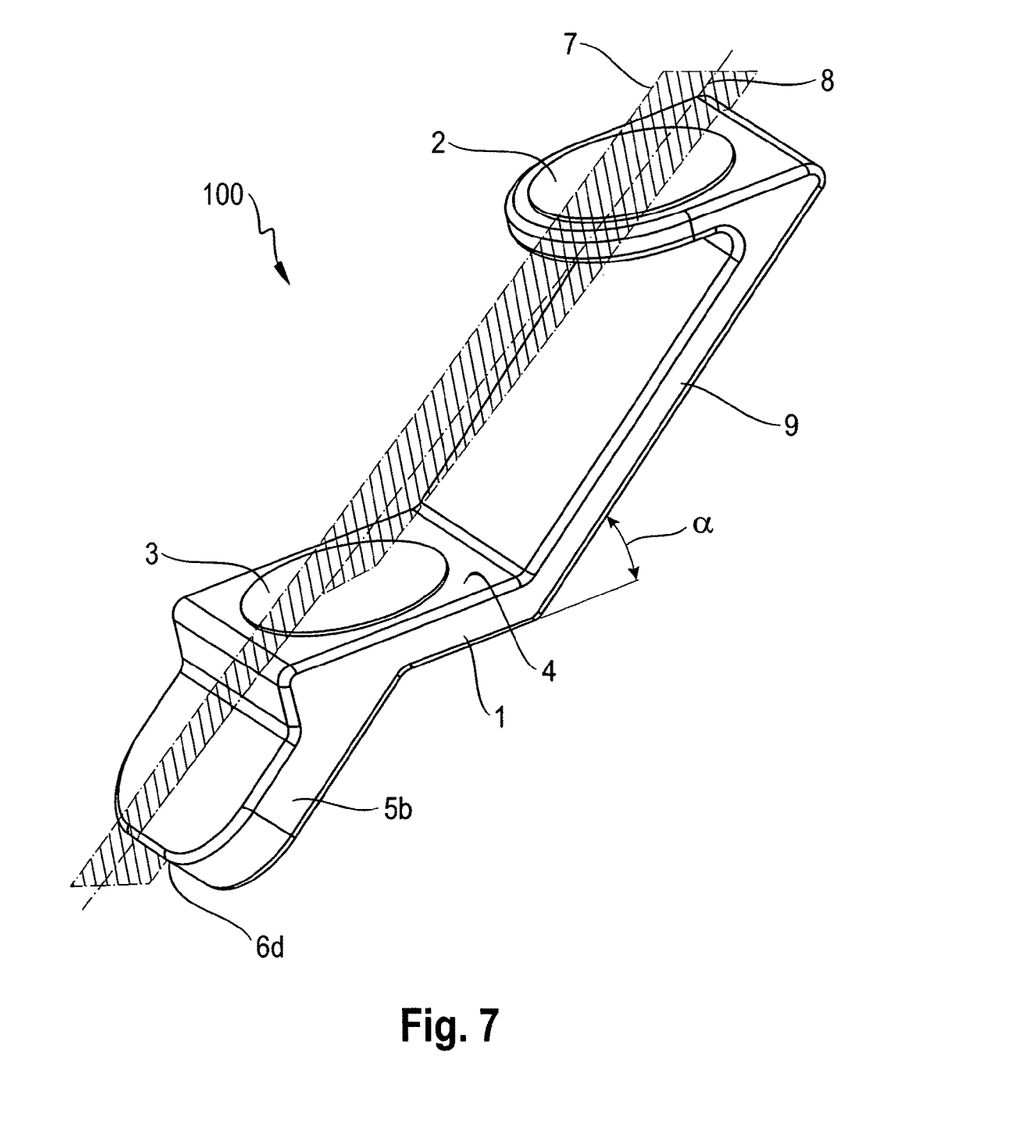
FIG. 7 shows a second embodiment of the marker device.

FIG. 7 shows a marker device 100 according to a second embodiment in which the same reference signs as in FIG. 1 devote the parts of the marker device 100 of the second embodiment which correspond to the respective parts of the marker device 10 of the first embodiment. In the second embodiment, the marker surface 4 is tilted relative to the trace 8 of the mirror plane 7 by an angle α which is greater than 0° and less than 90°. A first marker 3 is disposed in the marker surface 4, a second marker device 2 is disposed on a part of a marker carrier extension 9 which is disposed parallel to the marker surface 4. The attaching unit 5b is formed as a protrusion which runs substantially parallel to the extension part of the marker carrier extension 9 such that the longitudinal axis of the clearance 6d for attaching, in particular inserting, a marker holder 9 again lies symmetrically on the mirror plane 7.

Figure 8A:
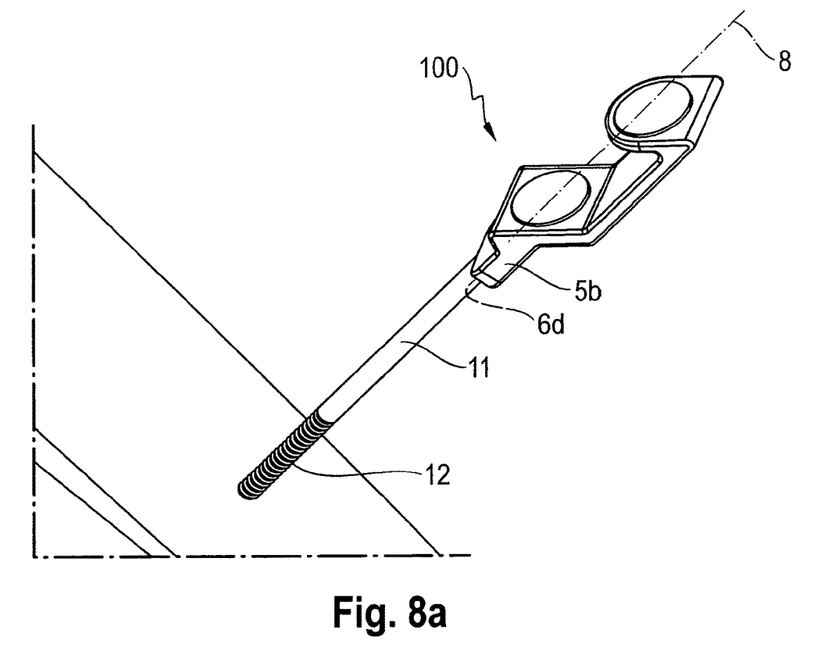
FIG. 8a shows a marker system comprising a marker device according to the second embodiment and a marker holder.

FIG. 8a shows a marker device 100 according to the second embodiment attached to a marker holder 11 of elongate shape which comprises an external thread 12 for attachment to an object such as an anatomical body part or a connecting device such as a non-invasive bracelet attached to an anatomical body part (e.g. a limb), which bracelet may for example have a corresponding (internal) counter thread. The longitudinal axis 8 of the marker holder 11 lies in the mirror plane of symmetry with respect to which the markers 2, 3 are arranged symmetrically.

Figure 8B:
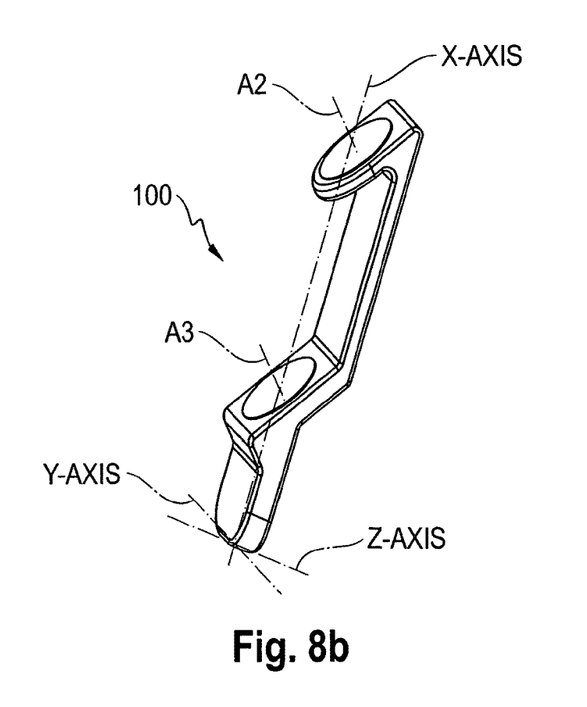
FIG. 8b shows the marker device of the second embodiment from a second perspective.

FIG. 8b shows the marker device 100 of the second embodiment from another perspective which makes clear that the marker surface 4 and the marker support for the second marker 2 and therefore the first and second planar markers 3, 2 are disposed parallel to each other.

Figure 9:
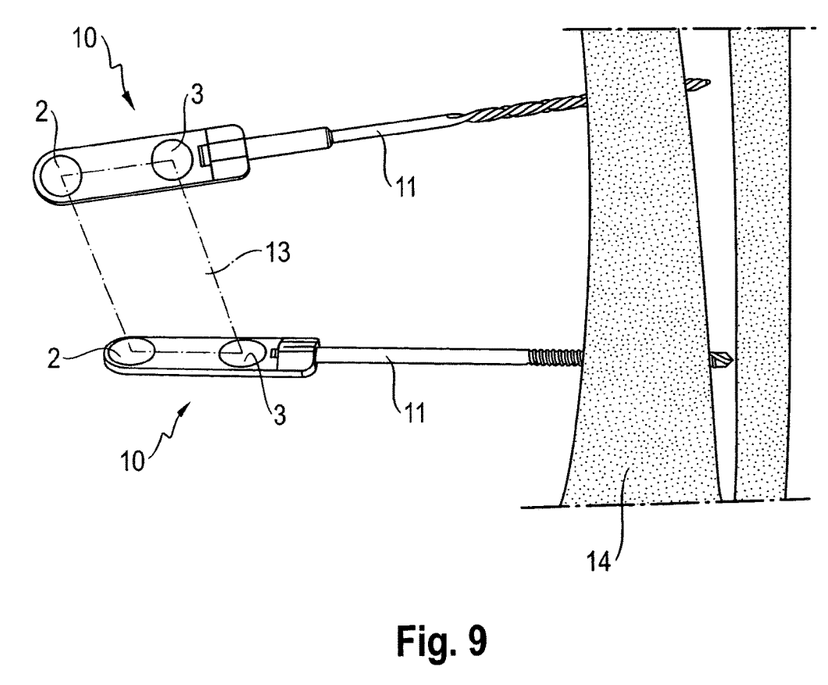
FIG. 9 shows how to construct a reference plane for position and spatial orientation determination of an object using two marker systems according to the invention.

FIG. 9 shows how two marker systems each comprising a marker device 10 of the first embodiment (which may be equally replaced by a marker device 100 of the second embodiment) are attached to marker holders 11 which in turn are fixed to an anatomical body part 14. The centre of each marker 2, 3 on each of the marker devices 10 defines a corner of a rectangular reference frame 13 which is used as a basis for determining a reference plane with regard to which positions and orientation in a navigated medical procedure can be defined.

Figure 10:
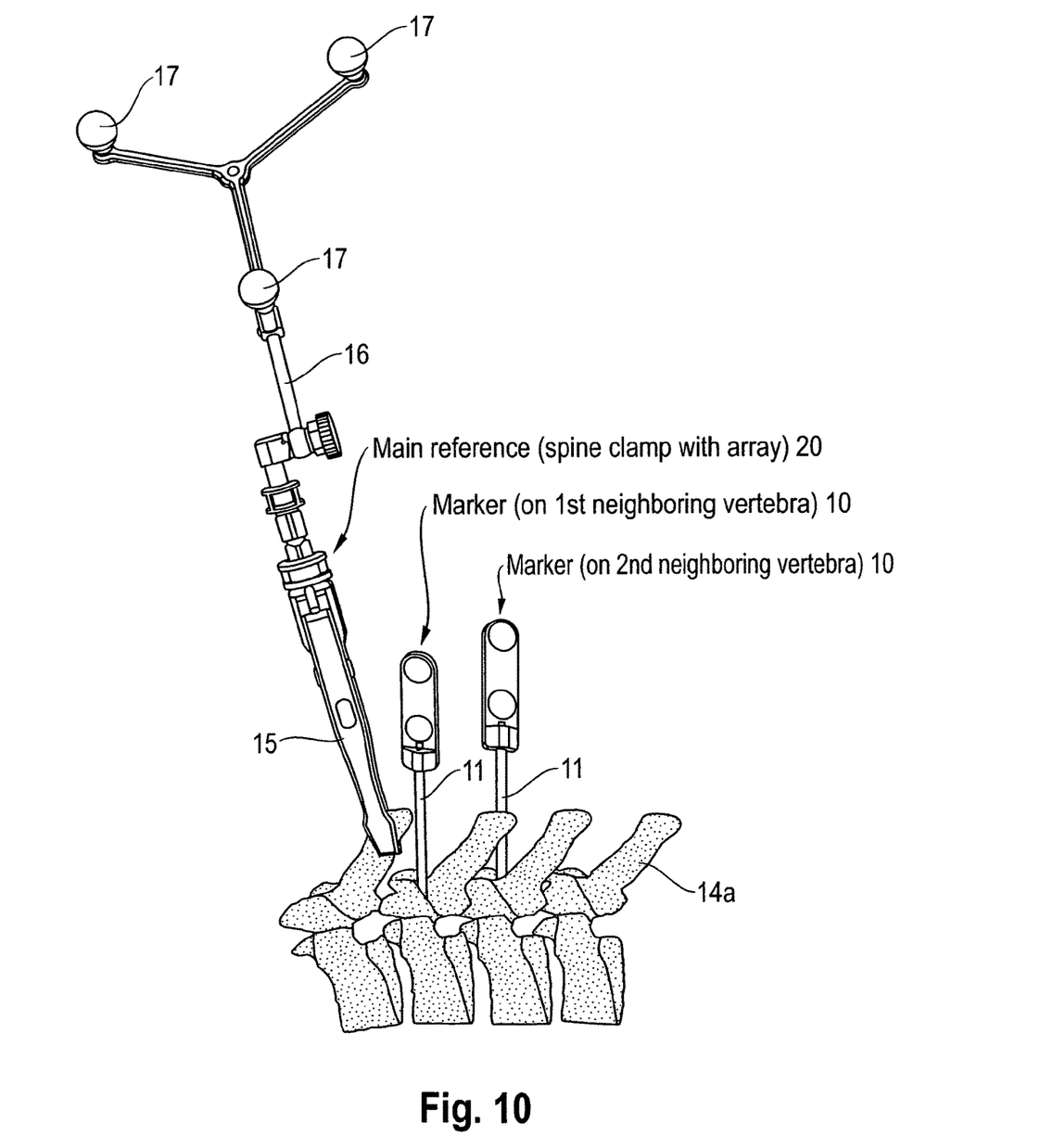
FIG. 10 shows the basic idea of progressive referencing of vertebrae.
Figure 13:
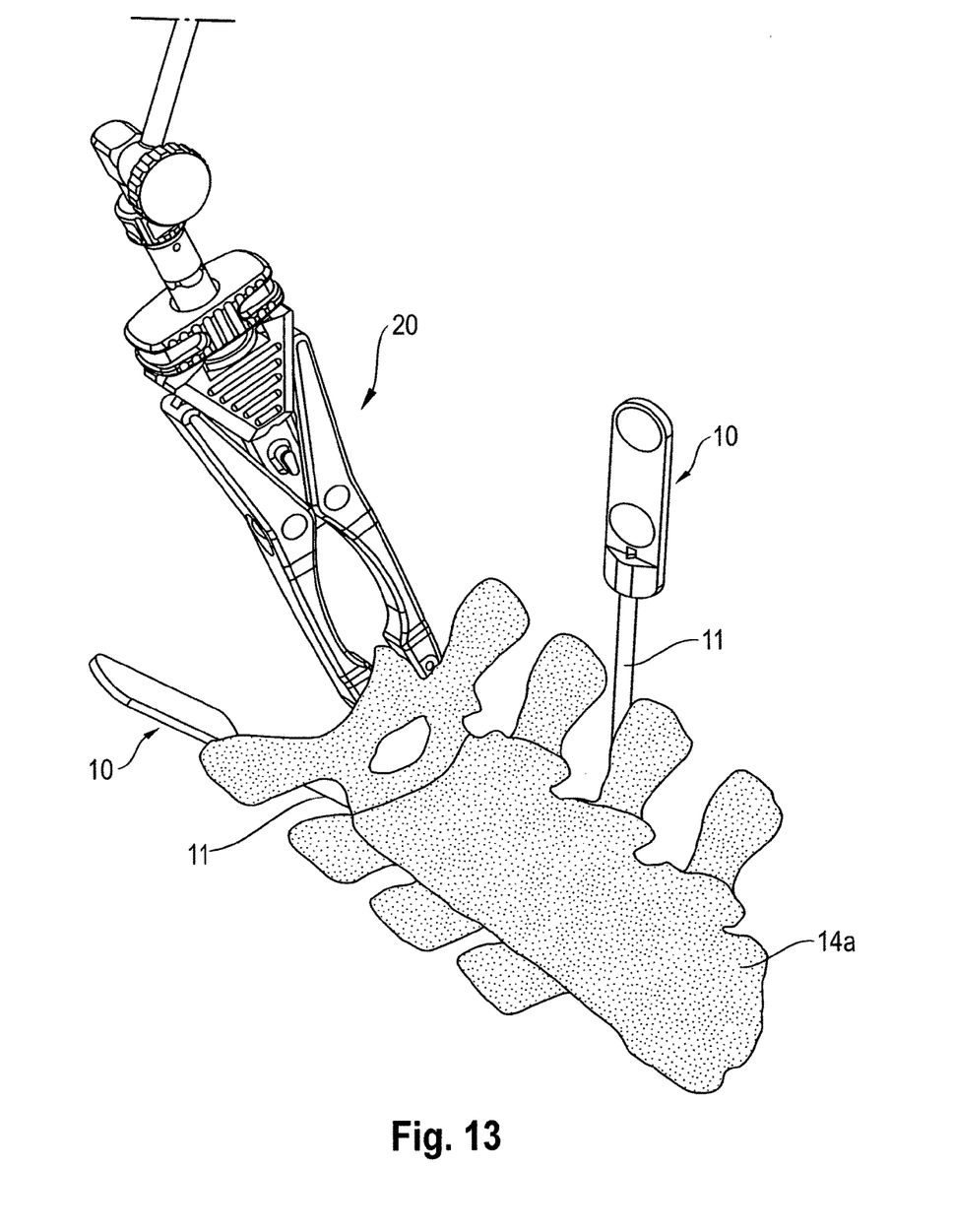
FIG. 13 shows the setup of FIG. 10 from a different perspective.

FIG. 10 shows a basic setup for referencing an anatomical body part 14a represented by vertebrae of the spine in which a reference star 16 having three individual circle markers 17 is attached by means of a holding device 20 comprising a clamp 15 for clamping a vertebraic processus. The position of the processus may be determined in a navigated procedure based on a predetermined and preferably fixed position of the processus relative to the reference star 16. Two marker systems comprising a marker device 10 and a marker holder 11 are disposed with the marker holder 11 in the base of vertebraic processi of the first and second neighbouring vertebrae on each a different side of a straight line defined by the spinal processi, i.e. one of the marker devices 10 defines a position on the right side of the spinal processus and the other marker device 10 defines a position on the left side of the spinal processus. This is also illustrated by FIG. 13 which gives a better perspective for illustrating the setup of the marker systems relative to a central axis of the spine.

Figure 11A:
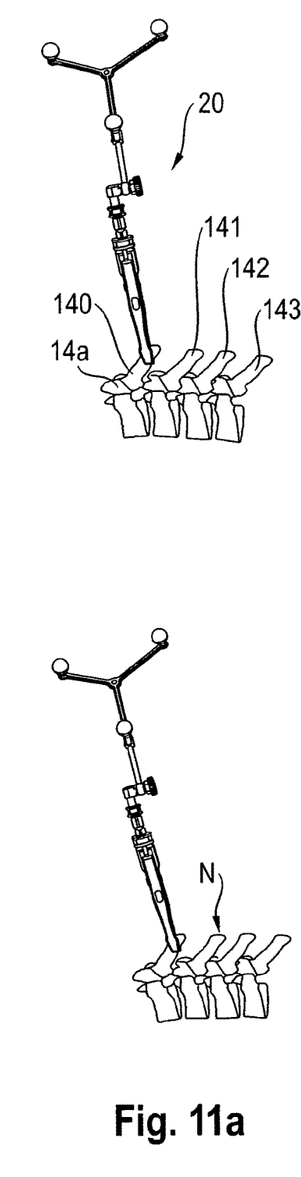
FIGS. 11a to 11c show the different steps of the method according to FIG. 10.
Figure 11B:
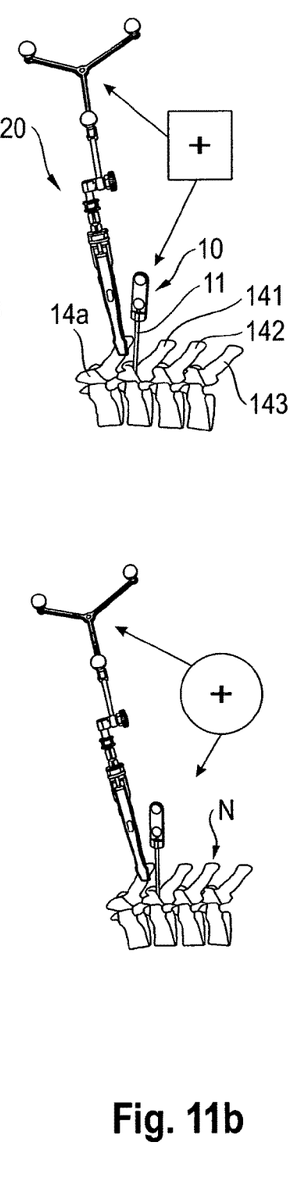
Figure 11C:
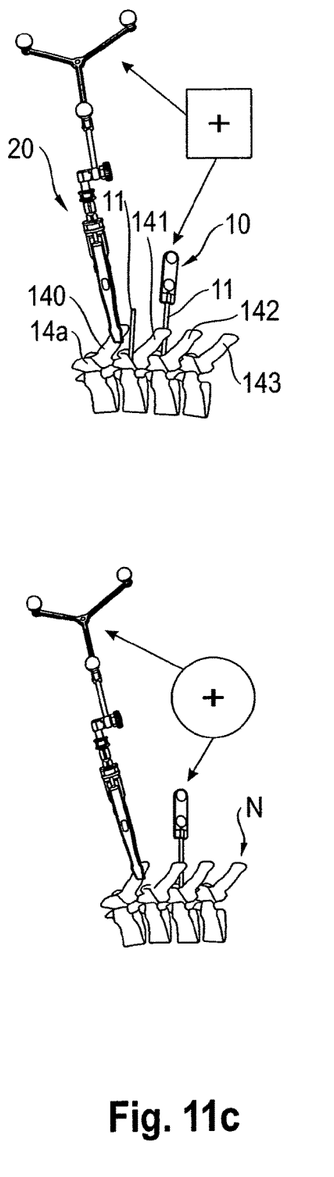

FIGS. 11a to 11c give an impression of how to conduct a method of referencing a plurality of vertebrae using the setup of FIG. 10. According to FIG. 11a, the reference star system 20 is attached to an initial vertebrae 140, the position of which may be determined by using the reference star system 20. The position of the first neighbouring vertebra 141 may also be determined based using the reference star system 20 by applying known anatomical relationships between the initial vertebrae 140 and the first neighbouring vertebra 141. The measurement error associated with determining the position of the other vertebrae based on the known position of a neighbouring vertebrae is negligible. However, moving the reference star system 20 further along the spine for example to the first neighbouring vertebra 141 or the second neighbouring vertebra 142 would be associated with major medical complications. It therefore appears sensible to use the inventive small-size marker system comprising a marker device 10 for determining the position of the second neighbouring vertebra 142 based on the known position of the first neighbouring vertebra 141.

FIG. 11b shows an example of attaching an inventive marker system a marker device 10 with a marker holder 11 to the base of the first neighbouring vertebra 141 to give an exact determination of the position of the first neighbouring vertebra 141 from which the position of the second neighbouring vertebra 142 can be determined. This process is then continued for the third neighbouring vertebra 143 by attaching a further inventive marker system to the base of the second neighbouring vertebra 142 and determining the position of the third neighbouring vertebra 143 based on the position measurement of the further inventive marker system or the base of the second neighbouring vertebra 142, respectively. The marker holder 11 which was attached to the base of the first neighbouring vertebra 141 may for example be left at its location, while the marker device 10 associated to the marker holder 11 may be removed. To this end, it is suitable to have an attaching unit 5 which enables simple attachment and removal of the marker device 10, 100 to and from the marker holder 11. The marker holder 11 left in the first neighbouring vertebra 141 may for example be used to guide an implant, in particular for placing cannulated screws in the first neighbouring vertebra 141. For example, a cannulated screw may be pushed over the marker holder 11 in order to be placed at the well-defined position of the marker holder 11.

Figure 12A:
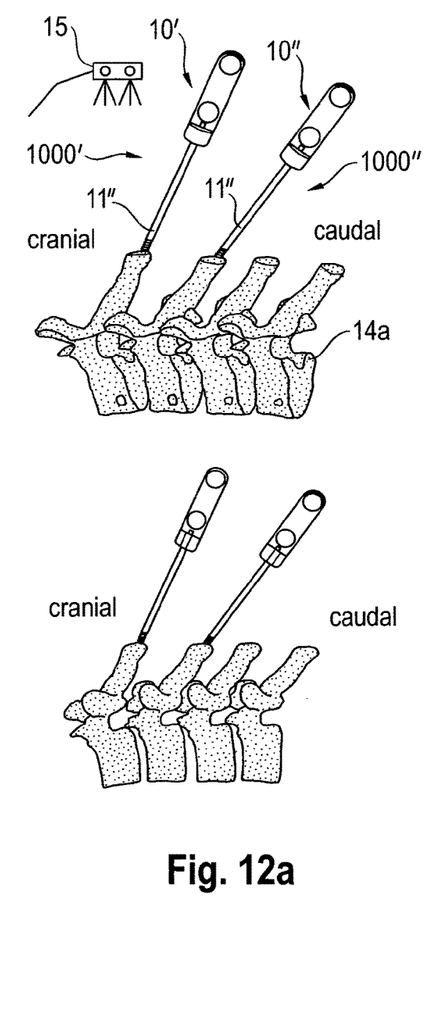
FIGS. 12a and 12b show the advantages of the inventive marker device when using it with a changing operation room setup.
Figure 12B:
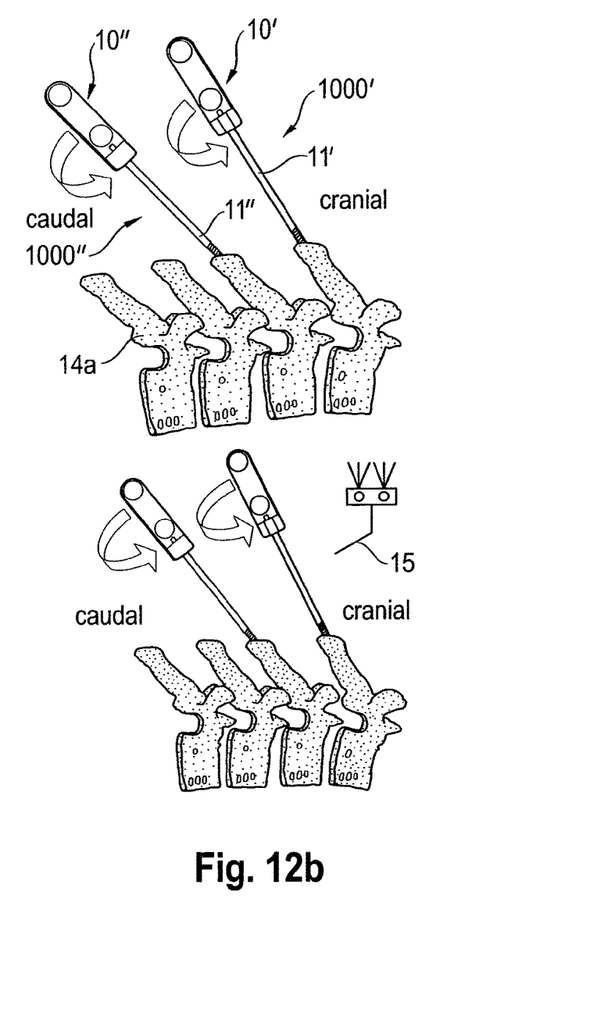

FIGS. 12a and 12b illustrate a specific advantage of the present invention, namely that the marker devices 10 may be rotated around the longitudinal axis of the marker holder 11 after being fixed to an anatomical body part 14a, in this case to each a spinal processus. In the setup of FIGS. 12a and 12b, a first marker system 1000' comprising a first marker device 10' and a first marker holder 11' and a second marker system 1000'' comprising a second marker device 10'' and a second marker holder 11' are attached to each and individual spinal process'. FIG. 12a shows that the first marker system 1000' is disposed on a spinal processus which is disposed more cranial than the spinal processors to which the second marker system 1000" is fixed. If now, for example, the position of the detection device 15 (such as a stereotactic camera) of a navigation system used to conduct the navigated medical procedure is moved to the other side of the patient, it may become necessary to adjust the position of the markers 2, 3 such that they can be viewed again by the detection device. FIG. 12*b* shows how this may be implemented by using the first and second inventive marker systems 1000', 1000". In order to position the markers 2, 3 into the viewing area of the detection device 15, the marker devices 10', 10" may be simply rotated around the longitudinal axis of the first and second marker holders 11', 11". In particular, the fit between the attaching units 5 of the first and second marker device 10', 10" at the insertion ends of the first and second marker holders 11', 11" may be lose enough to allow such a rotation while ensuring a correct positioning of the first and second marker devices 10', 10" on the first and second marker holders 11', 11" as long as no external forces are applied to the first and second marker holders 11', 11" and/or the first and second marker devices 10', 10". Alternatively or additionally, the fit between the attaching units 5 and the incision ends may be tight to prevent such a rotation. In that case, the whole marker system 1000', 1000" would have to be rotated, in particular, the marker holder 11', 11" would have to be wound into or out from the anatomical body part 14*a*, in order to adapt their orientation to the viewing field of the detection device 15.

As a further embodiment of the invention, markers may be located on both sides of the marker carrier 1 such that the rotation describing connection with FIGS. 12*a* and 12*b* may be reduced while maintaining the possibility of simple adaption of the orientation of the markers 2, 3 to the viewing direction of the detection device 15.

The invention claimed is:

1. A medical marker device, comprising:
   a) a plurality of markers each having a planar marker surface, wherein the plurality of markers are each disposed on the marker device such that each marker of the plurality of markers displays mirror symmetry with respect to a mirror plane of symmetry which is common to each marker of the plurality of markers, and wherein the planar marker surfaces are disposed in the same orientation relative to a marker plane which is normal to the mirror plane of symmetry and to the surface normal of each of the marker surfaces; and
   b) an attaching unit for attaching the marker device to a marker holder having an elongate shape, wherein the attaching unit is disposed on the mirror plane of symmetry such that a longitudinal axis of the marker holder lies in the mirror plane of symmetry when the marker device holder is connected to the attaching unit;
   wherein the marker plane is tilted relative to the longitudinal axis of the marker holder at an angle of between 0° and 90°, excluding these values, when the marker device is attached to the marker holder, and wherein at least one of the markers is not disposed in the marker plane, and at least one of the markers is disposed in the marker plane.

2. The marker device according to claim 1, wherein the markers are oriented in a same direction.

3. The marker device according to claim 1, wherein the markers have a round or polygonal circumference.

4. The marker device according to claim 1, wherein at least one of the markers is disposed in a plane that is parallel to the marker plane.

5. The marker device according to claim 1, wherein the markers are disposed on a planar marker carrier.

6. The marker device according to claim 1, wherein the attaching unit comprises a recess or clearance for receiving the marker holder.

7. The marker device according to claim 6, wherein the recess or clearance has a circular cross-section or a cross-section showing corners or angles.

8. A marker system comprising:
   a) the marker device according to claim 1, and
   b) the marker holder configured to be connected with the attaching unit of the marker device.

9. A data processing method of determining a reference plane in a navigated medical procedure, the data processing method being executable by a computer and comprising:
   a) acquiring marker position data comprising marker position information describing the position of at least three markers of two marker devices according to claim 1;
   b) determining, based on the marker position data, reference plane data comprising reference plane information describing a reference plane comprising the positions of the at least three markers.

10. A program which, when running on a computer or when loaded onto a computer, causes the computer to perform a data processing method of determining a reference plane in a navigated medical procedure, the data processing method comprising:
    a) acquiring marker position data comprising marker position information describing the position of at least three markers of two marker devices according to claim 1;
    b) determining, based on the marker position data, reference plane data comprising reference plane information describing a reference plane comprising the positions of the at least three markers.

11. A program storage medium on which the program according to claim 10 is stored in a non-transitory form.

12. A computer on which the program according to claim 10 is running or into the memory of which the program according to claim 10 is loaded.

* * * * *